United States Patent [19]

Suzuki et al.

[11] Patent Number: 5,463,431
[45] Date of Patent: Oct. 31, 1995

[54] PERIMETER

[75] Inventors: Takeshi Suzuki; Akihiro Sugiyama, both of Tokyo, Japan

[73] Assignee: Kabushiki Kaisha Topcon, Tokyo, Japan

[21] Appl. No.: 306,975

[22] Filed: Sep. 16, 1994

[30] Foreign Application Priority Data

Sep. 16, 1993 [JP] Japan .................................. 5-229935

[51] Int. Cl.⁶ ....................................................... A61B 3/02
[52] U.S. Cl. ........................... 351/226; 351/222; 351/224
[58] Field of Search ..................................... 351/224, 223, 351/222, 226

[56] References Cited

U.S. PATENT DOCUMENTS 5,235,360  8/1993  Minami .................................... 351/224

Primary Examiner—William L. Sikes
Assistant Examiner—Hung Xuan Dang
Attorney, Agent, or Firm—Finnegan, Henderson, Farabow, Garrett & Dunner

[57] ABSTRACT

A perimeter capable of objectively adding useful testing points without relying on an operator's intuitional judgment, and capable of performing a reliable test of the field of vision without imposing a useless burden on a subject. The perimeter includes a CPU 11 and a display portion 18. The CPU 11 forms data, which include estimated values, on a visual field characteristic distribution by making an interpolation between tested values of a subject's eye which are obtained by exhibiting a plurality of targets. The display portion 18 displays an unreliable distribution WP indicating a domain estimated to be distant from the tested values on the basis of data on the visual field characteristic distribution and data, which include the tested values, on a distribution of an estimated neighborhood of the tested values.

10 Claims, 11 Drawing Sheets

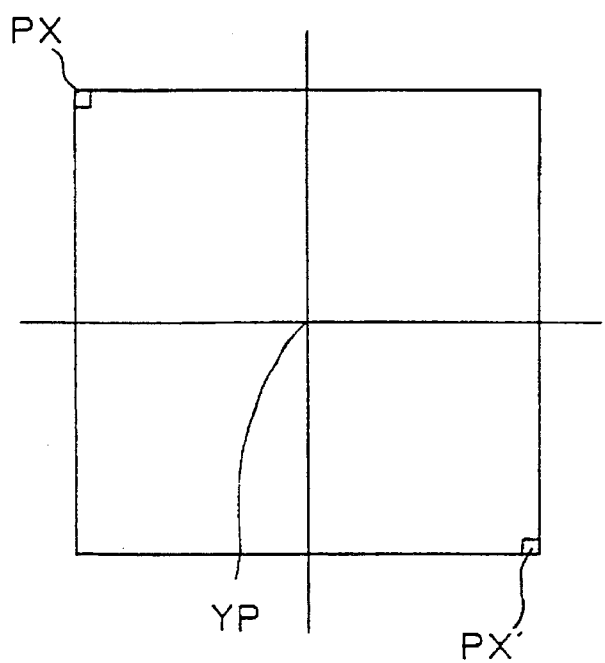 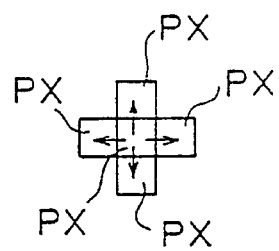
FIG.11(a)
FIG.11(b)

⟨NUMBER OF PEAKS⟩
i=1, NUMBER OF ADD-POINT=7
i=2, NUMBER OF ADD-POINT=1
i=3, NUMBER OF ADD-POINT=1
i=4, NUMBER OF ADD-POINT=1

PERIMETER

BACKGROUND OF THE INVENTION

1. Field of the Invention

The present invention relates to an improvement in a perimeter used to test a visual field.

2. Description of the Prior Art

Heretofore, there has been known a perimeter for testing functions of a retina or optic nerves of a subject's eye. In this type of perimeter, a plurality of targets are exhibited to the eye to test so-called kinetic and static visual fields.

In the visual field test, a screening test is first made in order to test the visual fields effectively and in a short time, and then, based on the results of the screening test, testing points are added for precise tests.

However, in this type of conventional perimeter, the testing points are added using, for example, a light pen manually and on operator's intuitional judgment. Therefore, there is a problem in that the testing points cannot be added effectively and in a short time if an operator is unskilled.

A perimeter also has been known in which testing points are automatically added. However, in this conventional perimeter, when a tested value is less than a predetermined value, the tested value is regarded as an isolated defective point, so that testing points are automatically added in the neighborhood of the defective point. For this reason, too many testing points are liable to be added. Further, a case also occurs in which testing points that do not contribute to the actual testing of the visual field are added. Consequently, a useless burden is unfavorably imposed on a subject.

SUMMARY OF THE INVENTION

It is, therefore, an object of the present invention to provide a perimeter capable of adding objectively useful testing points without relying on operator's intuitional judgment, and capable of trustworthily testing the field of vision without imposing any useless burden on the subject.

To achieve the above object, the perimeter according to the present invention comprises a portion for interpolating respective tested values of a subject eye obtained by exhibiting a plurality of targets to the eye and forming visual field characteristic distribution data which include estimated values and a portion for displaying an unreliable distribution which denotes an area estimated to be distant from the tested values on the basis of both data concerning an estimated distribution neighboring to and including the tested values and data concerning a visual field characteristic distribution.

According to the perimeter of the present invention, an unreliable distribution estimated to be distant from actually tested values of the visual field characteristic data can be objectively determined without relying on operator's intuitional judgment and without including an area useless for testing.

The perimeter according to the present invention further comprises a portion for determining additional testing points where an additional test of the visual field is carried out according to the unreliable distribution.

According to the perimeter, reliable tests of the field of vision can be carried out without adding useless testing points and, in addition, a burden imposed on the subject can be reduced.

BRIEF DESCRIPTION OF THE DRAWINGS

FIG. 8(a) is an offset coordinate system, FIG. 8(b) is a meridian direction coordinate system, FIG. 8(c) is a Y direction coordinate system, and FIG. 8(d) is an optic nerve fiber coordinate system.

FIG. 10(a) is an unreliable distribution expressed by gray-scale values, and FIG. 10(b) is an unreliable distribution expressed by numeric values.

FIGS. 11(a)–11(b) are drawings for describing the separation of the unreliable distribution into groups according to the present invention. FIG. 11(a) is a descriptive drawing of a case where respective areas are expressed by picture elements, and FIG. 11(b) is a descriptive drawing of a processing method of judging whether neighboring picture elements belong to the same group.

DESCRIPTION OF THE PREFERRED EMBODIMENT

One embodiment of a perimeter according to the present invention will now be described with reference to the attached drawings.

Figure 1:
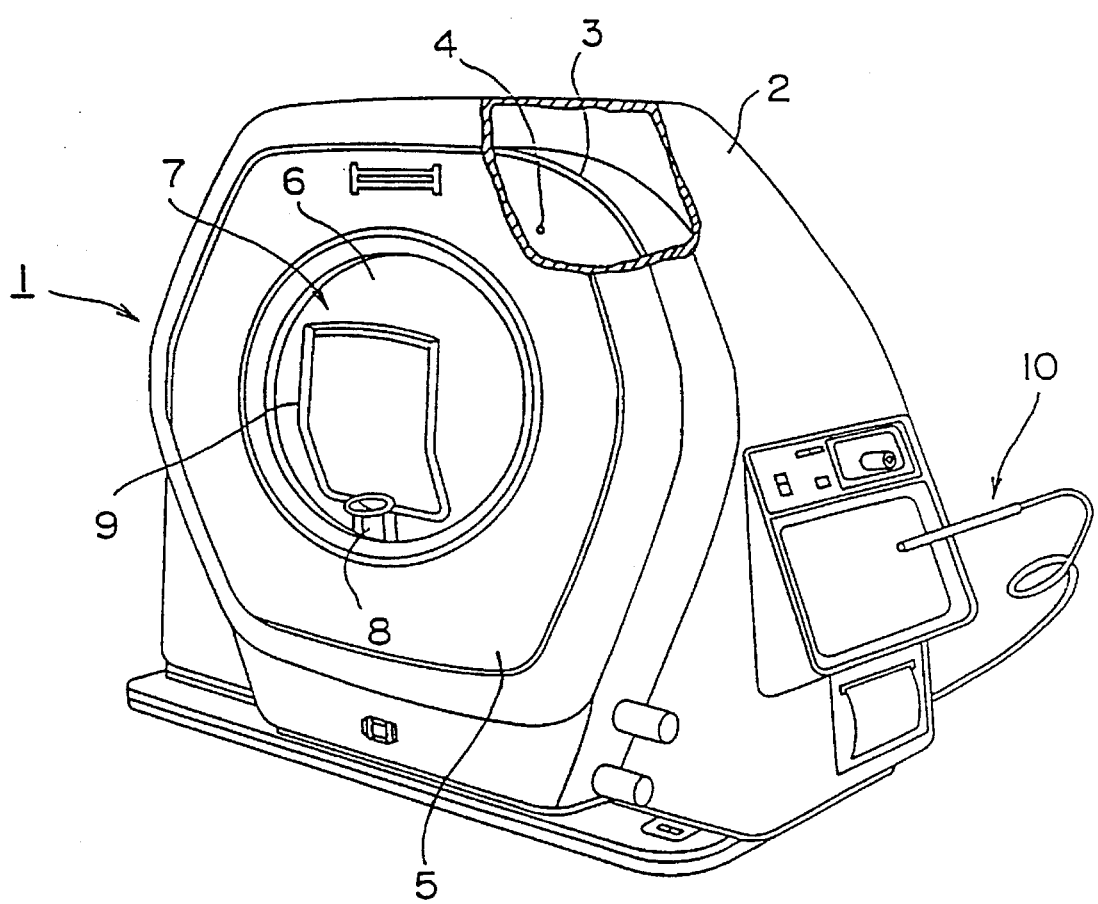
FIG. 1 is a perspective view showing an external appearance of a perimeter according to the present invention.

FIG. 1 is a perspective view showing a perimeter 1 according to the present invention. The perimeter 1 comprises a housing 2 and a semi-spherical dome 3. A spot 4 as a target is exhibited at a given place of an inner surface of the dome 3. A panel 5 is mounted on a front portion of the dome 3. An opening 6 adapted to receive a face of a subject is formed in the panel 5. A face receiving member 7 is formed in the opening 6. The face receiving member 7 includes a chin receiving portion 8 and a forehead receiving portion 9. When a test is carried out, subject's chin and forehead are pressed against the chin and forehead receiving portions 8 and 9, respectively. The subject discerns the exhibited spot 4 as a target while fixing the eyes upon a fixation target exhibited on the inner surface of the dome 3.

Figure 2:
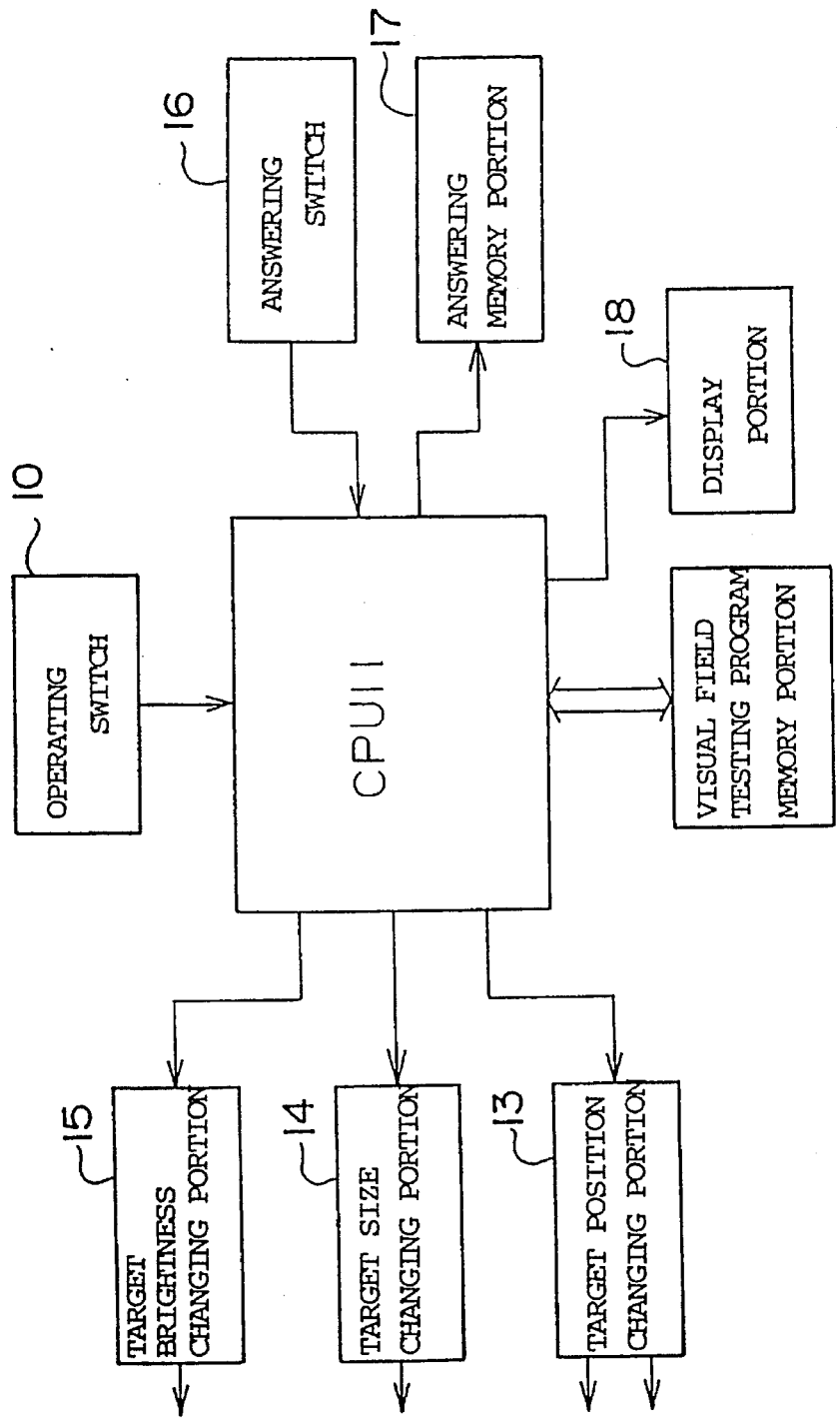
FIG. 2 is a block diagram of a control circuit of the perimeter according to the present invention.

An operator operates an operating switch 10 of, for example, a light pen in order to select the position (i.e., testing point), brightness, and size of a target to be exhibited and test a visual field. FIG. 2 shows a control block circuit for the test.

The control block circuit comprises a CPU 11, a visual field testing program memory portion 12, a target position changing portion 13, a target size changing portion 14, a target brightness changing portion 15, an answering switch 16, an answering memory portion 17, and a display portion 18. The CPU 11 performs various controls according to a command from the operating switch 10, a command from the answering switch 16, and a visual field testing program. The visual field testing program includes common visual field testing programs (a kinetic visual field testing program and a static visual field testing program), a quick screening test program, an unreliable distribution forming program, a testing point adding program, and so on.

When the brightness of a target to be exhibited is changed, the CPU 11 outputs a brightness changing signal to the brightness changing portion 15. When the size of the target is changed, the CPU 11 outputs a size changing signal to the size changing portion 14. Further, when the position (testing point) of the target is changed, the CPU 11 outputs a target position changing signal to the target position changing portion 13. In addition, the CPU 11 causes the answering memory portion 17 to memorize a tested value, which is a threshold value corresponding to a subject's answer made by operating the answering switch 16, in the answering memory portion 17.

In this embodiment, the threshold value is defined as a deviation between brightness (level of a quantity of light) obtained when the subject discerns an exhibited target and brightness (average level of a quantity of light) obtained when a normal person undergoes a visual field test. The latter brightness (average level) is fixed at "0". If a light quantity level at which the subject can discern an exhibited target at a testing point is high, the visual power of a retina of the subject's eye is low at the testing point.

Figure 3:
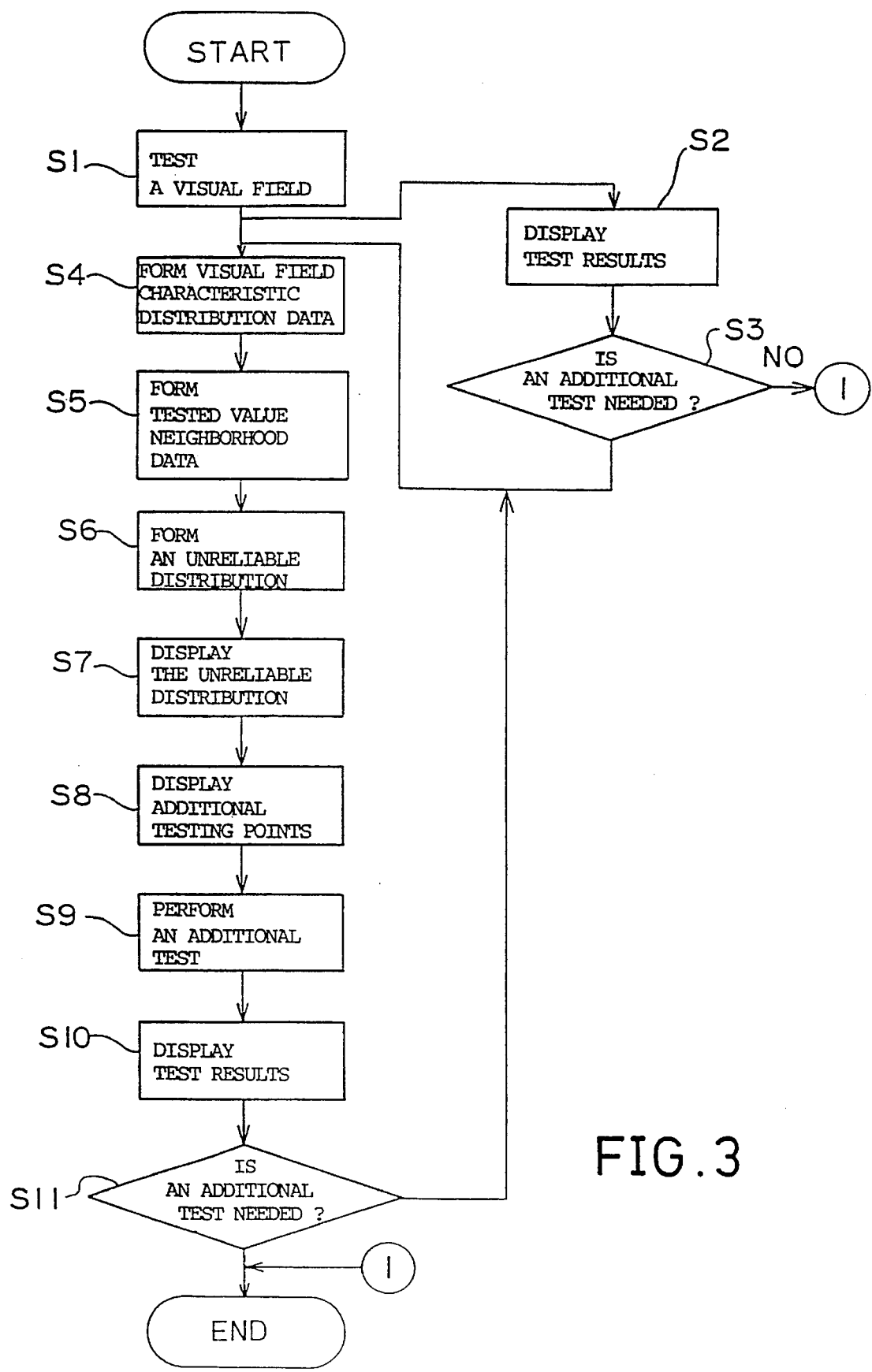
FIG. 3 is a flowchart showing steps of testing a visual field by means of the perimeter according to the present invention.
Figure 4:
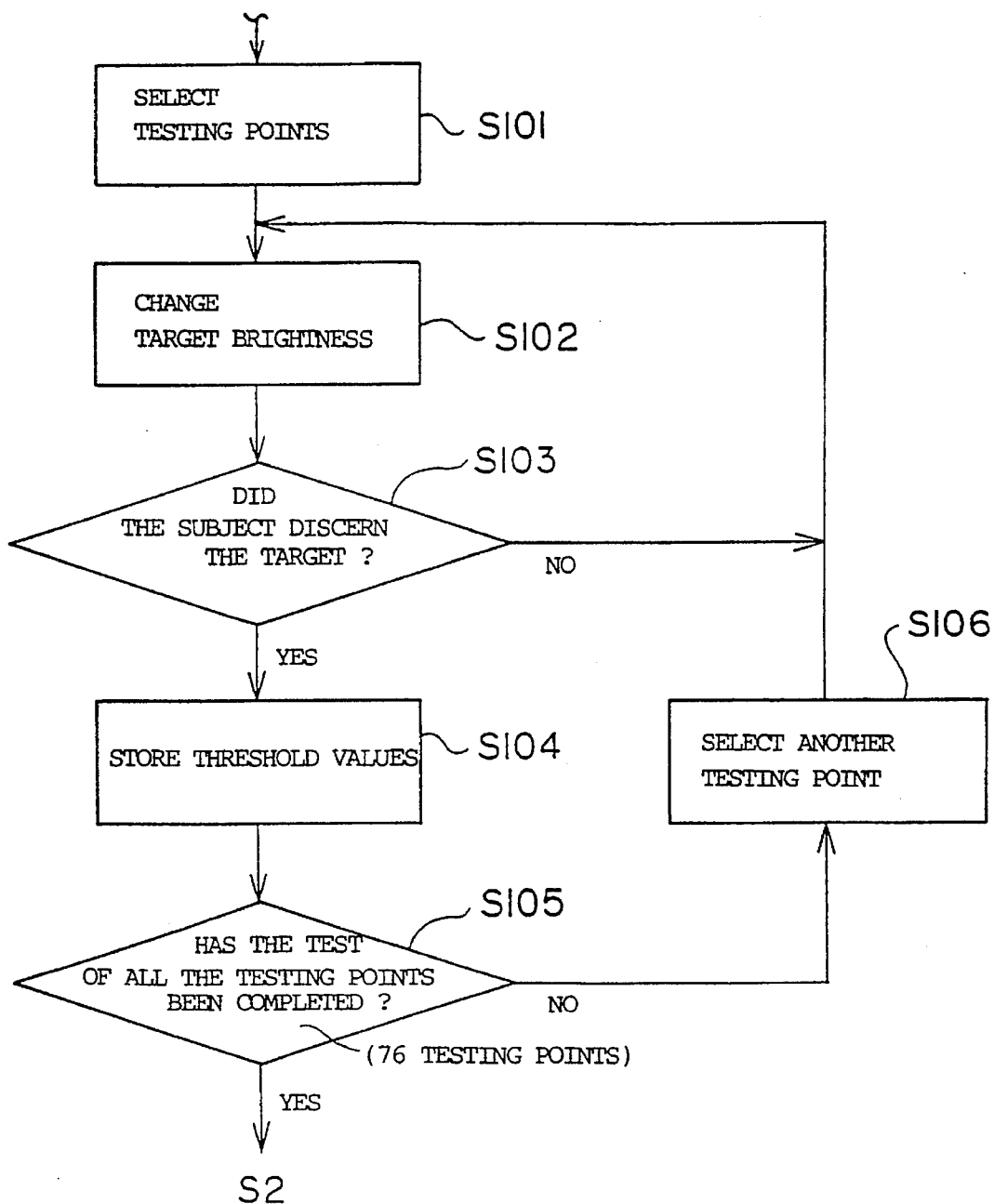
FIG. 4 is a flowchart showing details of S. 1 of FIG. 3.
Figure 5:
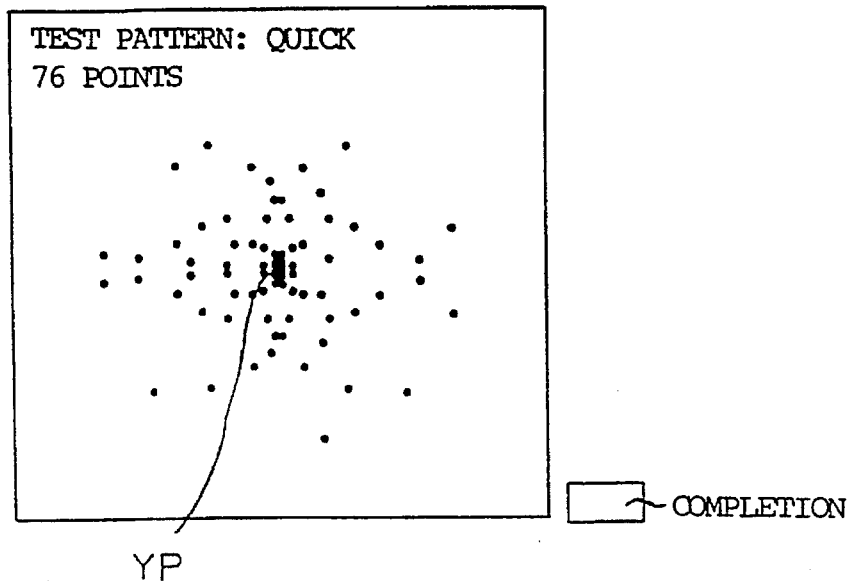
FIG. 5 shows one example of testing points of a screening test according to the present invention.

A quick screening test is first decided by the operator, and then, in S. 1 of FIG. 3, the visual field testing program is selected. FIG. 4 shows a detailed procedure of the program of S. 1. In S. 101, the CPU 11 selects testing points. The number of testing points exhibited in the quick screening test is 76. An example of the testing points is shown in FIG. 5. In this embodiment, the selected testing points are distributed within the circle of latitude 50° centering a macular portion YP.

Next, with respect to each of the testing points, brightness in which a normal person can discern a target is determined and the target is exhibited to the subject. The CPU 11 judges whether or not the subject can discern the target (S. 102 and S. 108). In S. 108, if a subject's answer is not received, the CPU 11 regulates the lightness of the target to intensify a brightness level (8. 102). In this embodiment, the brightness level is intensified 3 dB at a time. The CPU 11 repeats the steps of S. 102 and S. 103 until the answering switch 16 is operated. When the answering switch 16 is operated, the CPU 11 causes the answering memory portion 17 to memorize a threshold value as a tested value (S. 104). In this embodiment, the tested value is expressed as a deviation from the average light quantity level of the normal person.

Next, the CPU 11 judges whether or not the test of all of the 76 testing points has been completed (S. 105). If not, a following testing point at which the target is exhibited is indicated in S. 106, and the step shifts from S. 106 to 8. 102. Brightness in which the normal person can discern the target is again selected and the target is exhibited. The CPU 11 judges whether or not the subject can discern the exhibited target (S. 102 and S. 108). If a subject's answer is not received in S. 103, the CPU 11 regulates the lightness of the target to intensify a brightness level (S. 102). These steps are repeated until the exhibition of the target for all of the testing points is completed.

Figure 6:
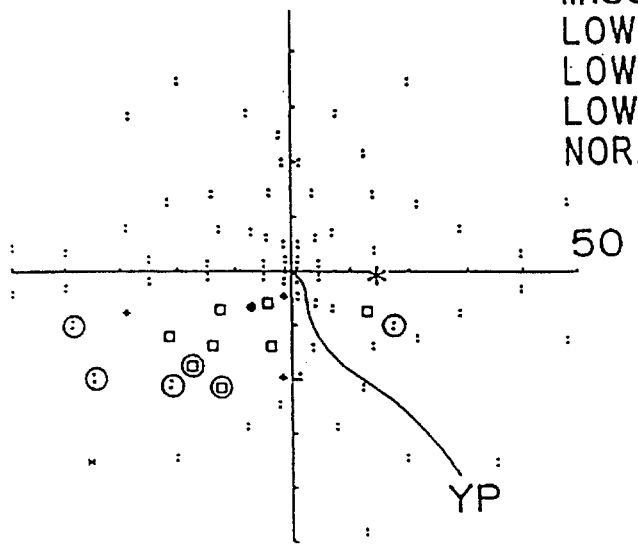
FIG. 6 shows one example of results of the screening test according to the present invention.

When the test of all the testing points is completed, the step shifts from S. 1 to S. 2. In S. 2, the CPU 11 causes the display portion 18 to display test results. A display based on a usual screening test is made on the display portion 18. FIG. 6 shows a test result displayed on the display portion 18. In FIG. 6, NORM means an average of threshold values of the normal person. LOW1 means that the lightness of the target is made larger than NORM by 3 dB in terms of voltages. LOW2 means that the lightness of the target is made larger than NORM by 6 dB in terms of voltages. LOW3 means that the lightness of the target is made larger than NORM by 9dB in terms of voltages. MISS means an impossibility of the test.

Figure 7:
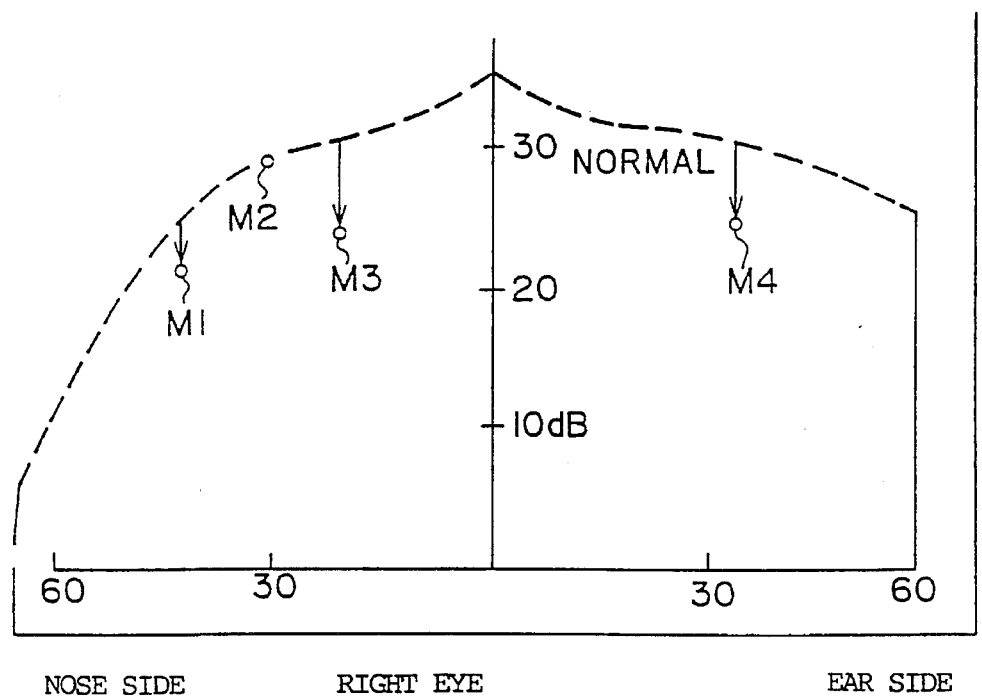
FIG. 7 shows one example of results of the screening test according to the present invention and shows a test result of a predetermined longitudinal direction of a subject.

FIG. 7 shows an example of tests in a longitudinal direction, being expressed by visual sensitivity. In FIG. 7, the broken line designates an average curve NORMAL of the threshold values at various parts of the retina of a normal eye. M1 to M4 designate data on the visual sensitivity of the subject's right eye. That is, the increase of a quantity of light of a target means that the visual sensitivity of a part of the retina of the subject's eye is low. A place which is lower in sensitivity than an area enclosing the place is defined as a defective point.

From the results of the screening test displayed on the display portion 18, the operator judges whether to add testing points (S. 3). In the case of no addition, the operator completes the test by operating an "N" of the operating switch 10. In the case of addition of the testing points, the operator operates a "Y" of the operating switch 10 to shift from S. 3 to S. 4.

In S. 4, the CPU 11 forms visual field characteristic distribution data based on the tested values. The data are formed according to a so-called spline interpolation method. The spline means an adjustable ruler. The spline interpolation method is an approximation technique in which a given interval is subdivided into some subintervals, a polynomial is applied to each of the subintervals so as to go through given points as a whole, and first and second differential coefficients are caused to coincide with each other at the given points. According to the spline interpolation method, a natural curve greatly fit for a human sensitivity can be obtained. Since the method is well known, a detailed description of it will be omitted.

Figures 8A, 8B, 8C:
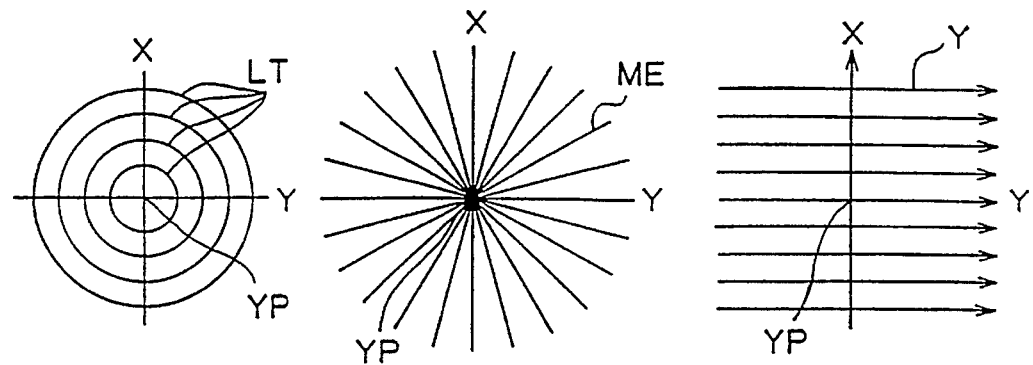
FIGS. 8(a)–8(d) illustrate coordinate systems of a spline interpolation method adopted to form data concerning a visual field characteristic distribution according to the present invention.
Figure 8D:
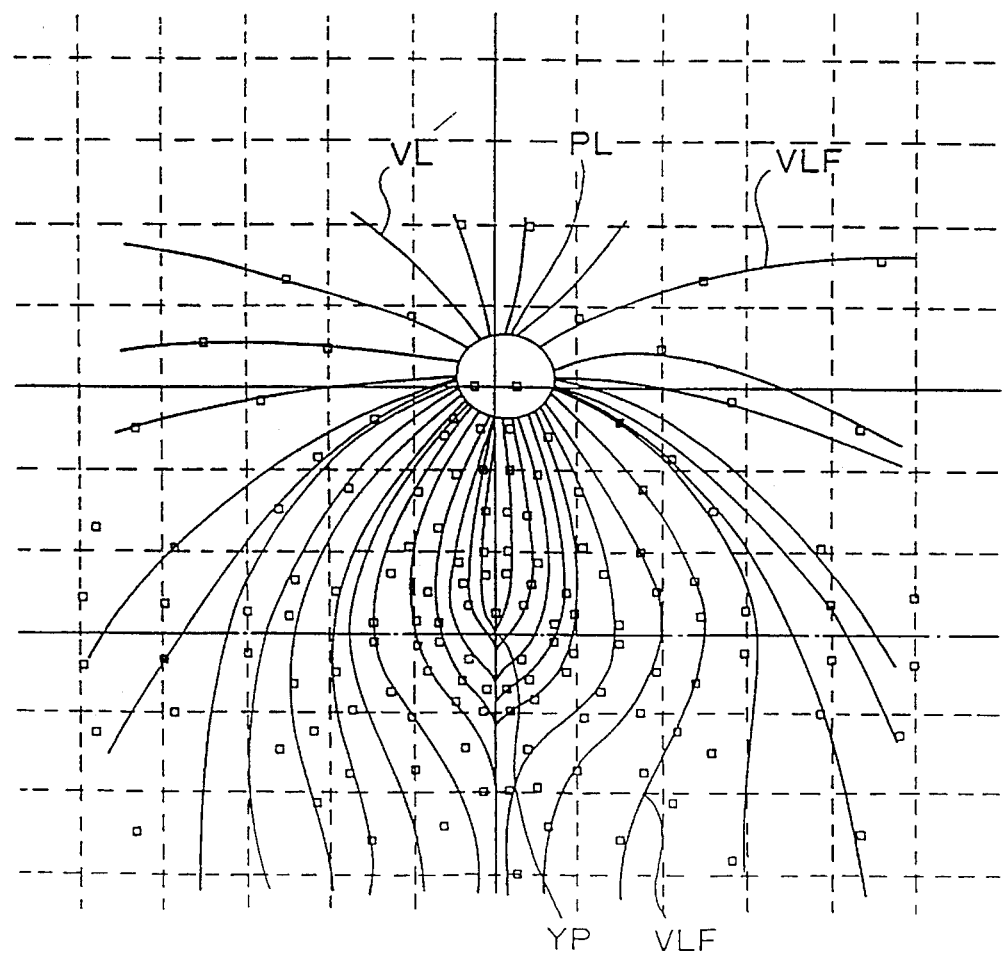

The spline interpolation method is carried out under an offset coordinate system (polar coordinate system) shown in FIG. 8 (a). The center of offset coordinates is a macular portion YP. Interpolations in a circumferential direction are first carried out in given circles of latitude LT by turns from the macular portion YP, and then interpolations in a longitudinal direction ME are carried out as shown in FIG. 8(b) and interpolations in a Y direction are carried out as shown in FIG. 8(c). As a result of the interpolations, meshes are formed. Accordingly, the CPU 11 three-dimensionally obtains data concerning the visual field characteristic distribution. FIG. 8(d) shows another interpolation method in which interpolations are carried out along the optic nerve fiber VLF. This is an interpolation method desirable medically because of the interpolations along the elongate direction of the optic nerve fiber VLF. In FIG. 8 (d), PL designates a papilla and □ designates a testing point.

Although tests are not actually carried out, the visual field characteristic distribution data include an area estimated to have a low visual sensitivity. Therefore, it is necessary to add to testing points in order to make an exact visual field test.

Figure 9:
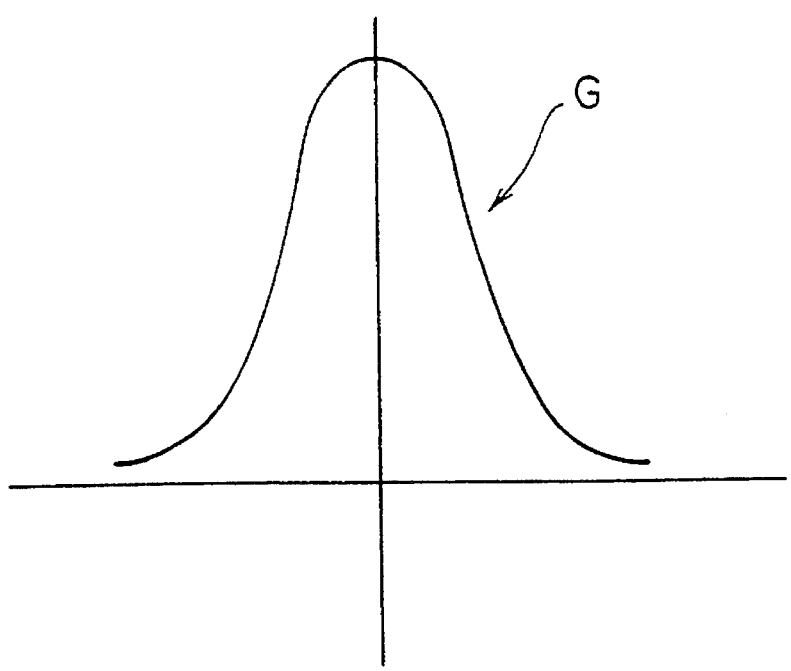
FIG. 9 shows a Gaussian distribution.

Next, in S. 5, the CPU 11 forms data concerning a neighborhood of the points of the tested values. The neighborhood including the actually tested points is considered to be shaped like a mountain according to a Gaussian distribution G shown in FIG. 9. Therefore, the tested value neighborhood data according to the Gaussian distribution G are formed by regarding each of the tested values as a peak (if the data are expressed by a human visual sensitivity, the depth of a trough is considered to conform to the Gaussian distribution G when a normal person's eye is made standard).

With respect to the 76 testing points, data concerning a neighborhood of the tested values are formed. After that, the CPU 11 subtracts the tested value neighborhood data from the visual field characteristic distribution data, thereby forming an unreliable distribution (S. 6). The unreliable distribution means a domain estimated to have a low visual sensitivity (low visual power) in appearance in spite of no performance of an actual test, in other words, it means a domain estimated to be deviated largely from the normal person. That is, a domain distant from the tested value neighborhood data and estimated to have a low visual sensitivity is unreliable. Therefore, in order to emboss the domain, an unreliable distribution is formed.

Next, the CPU 11 causes the display portion 18 to display the unreliable distribution WP (S. 7).

Figure 10A:
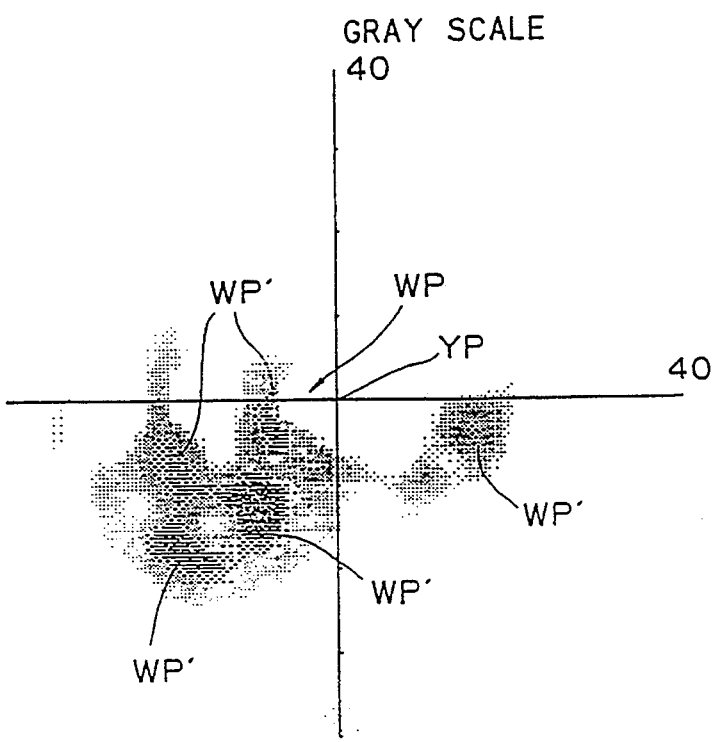
FIGS. 10(a)–(b) show unreliable distributions according to the present invention.
Figure 10B:
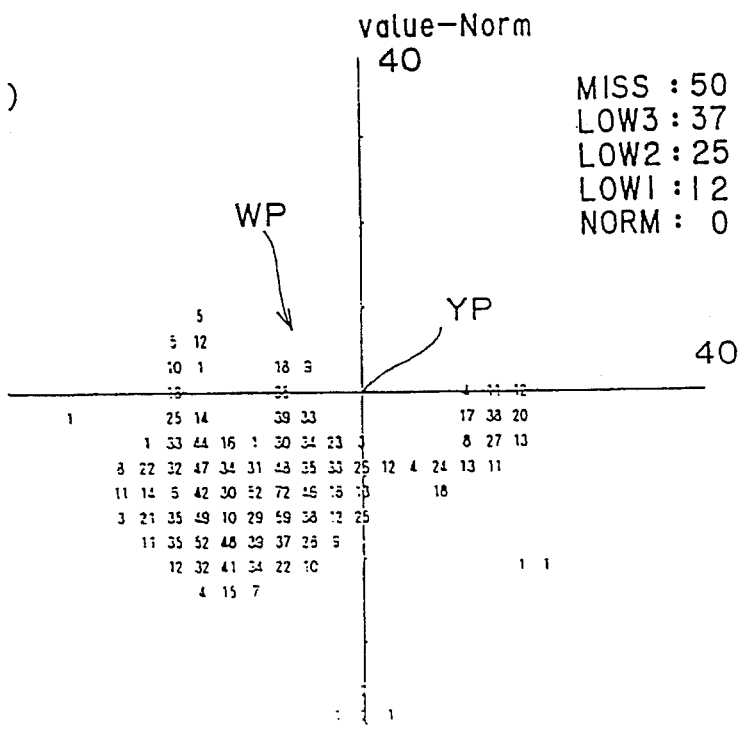

It is presumed that the whole of the visual field shown in FIG. 10(a) consists of 80×80 pixels (picture elements) PX in length and breadth as shown in FIG. 11 (a). The unreliable distribution WP is shown in a gray scale on the supposition that the pixels PX each have a gray-scale value corresponding to the unreliable distribution WP. In FIG. 10 (a), a dark portion WP' designates a portion lower in visual sensitivity than a portion surrounding the dark portion (in other words, a portion stronger in light intensity of a target than a portion surrounding the dark portion). FIG. 10 (b) shows a numeric expression of the unreliable distribution WP. Numeric values corresponding to NORM, LOW 1, LOW 2, LOW 3, and MISS are shown at the top right-hand corner of FIG. 10(b). NORM designates an average value of a normal person as mentioned above. A display of the unreliable distribution WP by such numeric values enables the operator to form a more objective judgment than a display of the same by a gray scale. If the unreliable distribution WP is displayed only by data obtained by subtracting the tested value neighborhood data from the visual field characteristic distribution data, domains regarded as noises are also displayed as an unreliable distribution. Therefore, the CPU 11 takes the following steps in order to eliminate the noises.

The CPU 11 first sums up gray-scale values of the pixels PX, and then the total value is divided by the number of the pixels PX. As a result, a threshold level SL is obtained. However, since a pixel corresponding to a testing point has a gray-scale value of "0", the pixel having the value "0" is not used for calculating the threshold level SL.

The CPU 11 selects only pixels PX having gray-scale values larger than the threshold level SL. This process is carried out from a pixel PX located at the top left-hand corner of the display to a pixel PX' located at the lower right-hand corner of the same. In this case, the CPU 11 compares pixels having gray-scale values larger than the threshold level SL with each other in every direction as shown in FIG. 11(b). If neighboring pixels PX each have a gray-scale value larger than the threshold level SL, the CPU 11 judges that these pixels belong to the same group and gives them the same numeric value.

Figure 12:
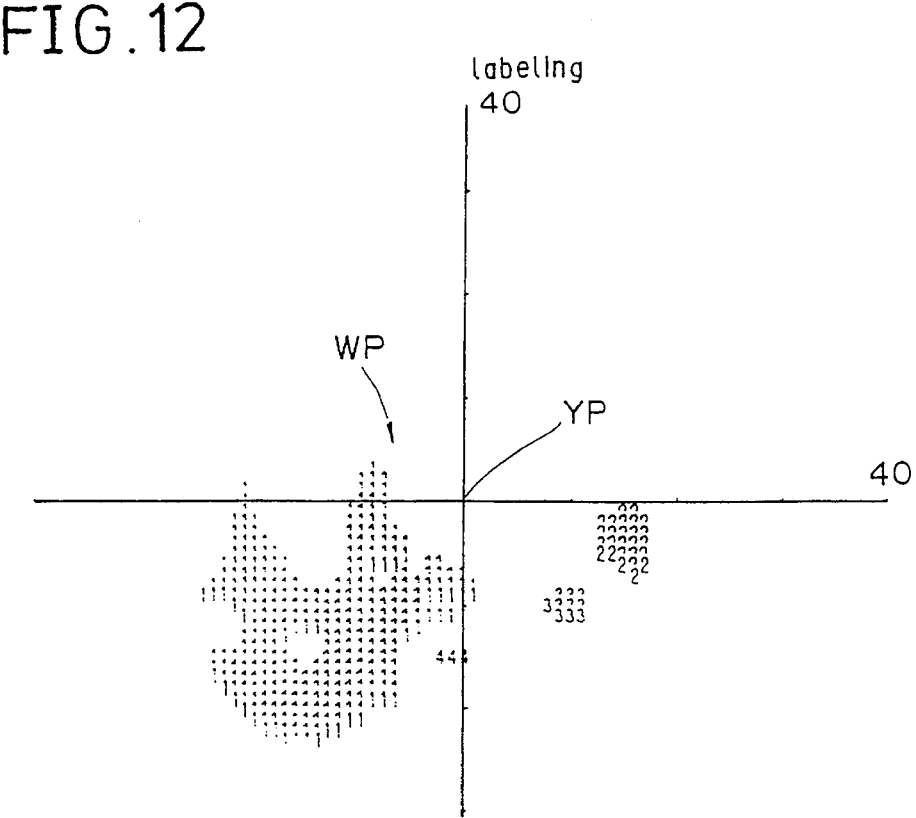
FIG. 12 shows an unreliable distribution separated into groups.

Thereby, as shown in FIG. 12, the unreliable distribution WP separated into groups is displayed. In FIG. 12, numerals "1" to "4" represent respective domains of the unreliable distribution separated into the groups. Next, the CPU 11 searches the unreliable distribution WP for pixels having a peak. In the search, the unreliable distribution WP is differentiated in X and Y directions. A point having differentiation value "0" in the two directions (a point where variation from positive to negative occurs) is a pixel having a peak.

Let it be supposed that domains "1" through "4" are obtained as shown in FIG. 12. In this case, the CPU 11 calculates a total of deviation within each of the domains, and then divides the total by the number of the pixels used for calculating the total to obtain an average value. For example, if an average value of domain "4" is 1, an average value of domain "3" is 1, an average value of domain "2" is 1, and an average value of domain "1" is 7, the ratio of the average values of domain "1" through domain "4" is expressed as "4":"3":"2":"1"=1:1:1:7. If the number of additional testing points is N, N/10 testing points, N/10 testing points, N/10 testing points, and 7N/10 testing points are allotted to domains "4", "3", "2", and "1", respectively. Thereby, the testing points are added to each of the domains in order of the largeness of a peak in the domain. For example, if N=10, one testing point is added to domains "4" "3" and "2" and seven testing points are added to domain "1".

Figure 13:
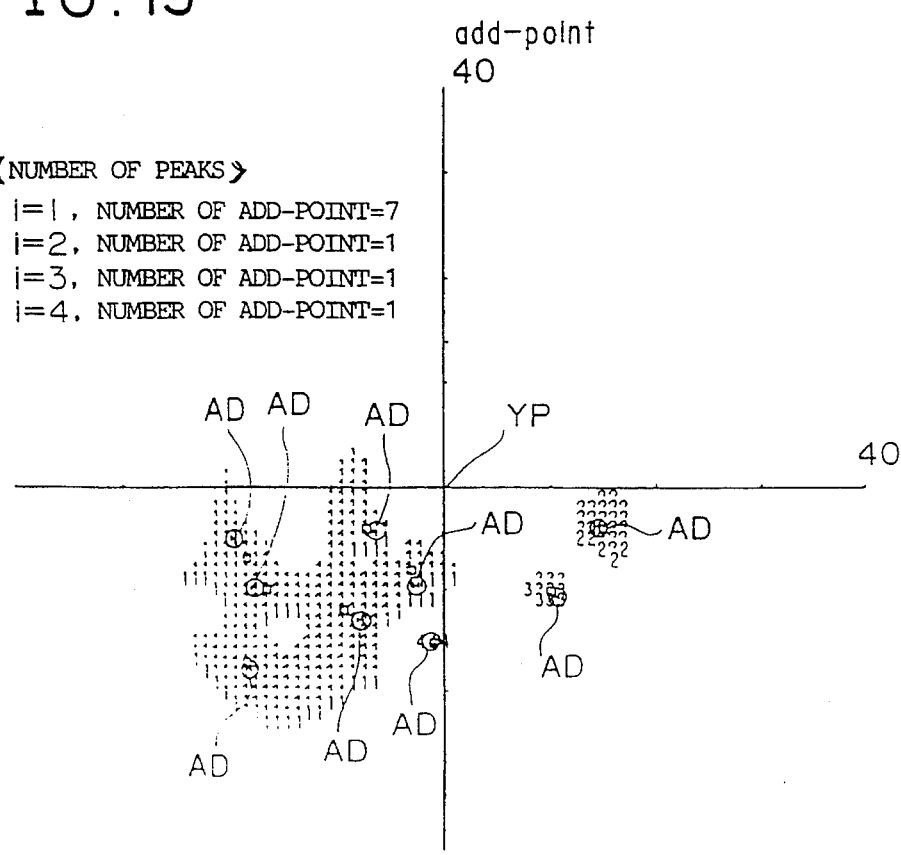
FIG. 13 is a descriptive drawing of the position and number of additional testing points.

The CPU 11 thus adds the testing points to the domains. The additional testing points are displayed as shown in FIG. 13 (S. 8). In FIG. 13, AD designates an additional testing point. The additional testing point AD is displayed in the neighborhood of a place having a peak value.

An example of a process of adding the testing points was mentioned above, but various testing point adding processes can be adopted as follows:

(a) The number of peaks within each of domains is first counted, and then the ratio of the number of peaks between the domains is calculated to determine the number of additional testing points for the respective domains. In each of the domains, the additional points are given in such a way that one of the additional testing points is first given to a place having the largest peak value and then another additional testing point is given to a place having the second largest peak value, and one after another.

(b) In each of the domains, only peak values are picked up to calculate their cumulative frequencies. The ratio of the cumulative frequencies is calculated, and the number of testing points to be added to each of the domains is determined from the resultant ratio.

(c) The largest peak value is selected from peak values of each of the domains. The ratio between the largest peak values of the respective domains is calculated to determine the number of testing points to be added to each of the domains.

After (a), (b), or (c), the CPU 11 causes a target to be exhibited at a place where an additional testing point is determined to be added, and performs the test (S. 9). The process of exhibiting the target is substantially similar to that shown in the flowchart of FIG. 4. When the test is completed, the CPU 11 causes results to be displayed (S. 11). The CPU 11 judges whether or not an additional test is needed. If needed, the step shifts from S. 11 to S. 4. If not needed, the test is completed. In the case of an isolated defective point, a few testing points are added in the neighborhood of the isolated defective point.

What is claimed is:

1. A perimeter comprising:

a portion for forming data concerning a visual field characteristic distribution in such a way that interpolations are made between tested values of a subject's eye which are obtained by exhibiting a plurality of targets, the visual field characteristic distribution including estimated values; and a portion for displaying an unreliable distribution which denotes a domain estimated to be distant from said tested values on the basis of both said data concerning the visual field characteristic distribution and data which include the test values, on a distribution of an estimated neighborhood of the tested values.

2. A perimeter comprising:

a portion for forming data concerning a visual field characteristic distribution in such a way that interpolations are made between tested values of a subject's eye which are obtained by exhibiting a plurality of targets, the visual field characteristic distribution including estimated values; and a portion for displaying an unreliable distribution which denotes a domain estimated to be distant from said tested values on the basis of both said data concerning the visual field characteristic distribution and data which include the test values, on a distribution of an estimated neighborhood of the tested values;

said perimeter further comprising a portion for determining additional testing points which are needed for additional visual field test according to said unreliable distribution.

3. A perimeter according to claim 2, wherein said visual field characteristic distribution data are formed by a spline interpolation method, a spline interpolation being a coordinate system along elongated directions of an optic nerve fiber bundle.

4. A perimeter according to claim 2, wherein said unreliable distribution is formed by data obtained by subtracting said tested value neighborhood data from said visual field characteristic distribution data.

5. A perimeter according to claim 4, wherein said tested value neighborhood data are formed according to a Gaussian distribution.

6. A perimeter according to claim 5, wherein said unreliable distribution is expressed in a gray-scale value of each of picture elements, said unreliable distribution being displayed in such a way that picture elements which coincide with testing points equal to gray-scale value 0 are eliminated, gray-scale values of the other picture elements are summed up, a total of the gray-scale values is divided by the number of said other picture elements in order to obtain a threshold value, and picture elements which have gray-scale values larger than an obtained threshold value are selected.

7. A perimeter according to claim 5, wherein said unreliable distribution is displayed in numeric values.

8. A perimeter according to claim 5, wherein said unreliable distribution is separated into groups, picture elements which have peaks within each of said groups are found out, and testing points are added to places located within each of said groups in order of largeness of peak values of the places.

9. A perimeter according to claim 8, wherein said testing points are allotted according to each of said groups.

10. A perimeter according to claim 5, wherein, if an isolated defective point exists, a plurality of testing points are added in the neighborhood of the isolated defective point.

* * * * *